US012564317B2

(12) United States Patent
Hallen et al.

(10) Patent No.: US 12,564,317 B2
(45) Date of Patent: Mar. 3, 2026

(54) SYSTEMS AND METHODS FOR LIGHT MODULATION DURING OPHTHALMIC SURGERY

(71) Applicant: Alcon Inc., Fribourg (CH)

(72) Inventors: Paul R. Hallen, Colleyville, TX (US); Mikhail Ovchinnikov, Dana Point, CA (US)

(73) Assignee: Alcon Inc., Fribourg (CH)

( * ) Notice: Subject to any disclaimer, the term of this patent is extended or adjusted under 35 U.S.C. 154(b) by 606 days.

(21) Appl. No.: 18/072,425

(22) Filed: Nov. 30, 2022

(65) Prior Publication Data

US 2023/0181025 A1     Jun. 15, 2023

Related U.S. Application Data

(60) Provisional application No. 63/265,156, filed on Dec. 9, 2021.

(51) Int. Cl.
A61B 3/00      (2006.01)
*A61F 9/007*      (2006.01)

(52) U.S. Cl.
CPC .......... *A61B 3/0008* (2013.01); *A61B 3/0025* (2013.01); *A61F 9/007* (2013.01)

(58) Field of Classification Search
CPC ..... A61B 3/0008; A61B 3/0025; A61B 90/30; A61F 9/007; A61F 9/0079; A61F 2009/00863; A61F 2009/00874; A61F 9/008
USPC ....................................................... 351/221
See application file for complete search history.

(56) References Cited

U.S. PATENT DOCUMENTS

| | | | | |
|---|---|---|---|---|
| 6,104,939 | A | * | 8/2000 | Groner ................. A61B 5/0261 |
| | | | | 382/134 |
| 8,511,824 | B2 | | 8/2013 | Saito |
| 10,881,550 | B2 | * | 1/2021 | Tedford ............... A61N 5/0613 |
| 2007/0051881 | A1 | * | 3/2007 | Ashdown .................. G01J 3/51 |
| | | | | 250/226 |
| 2008/0012997 | A1 | * | 1/2008 | Reuter ................. H04N 9/3111 |
| | | | | 348/E9.027 |
| 2009/0171327 | A1 | | 7/2009 | Goldstein |
| 2015/0136037 | A1 | * | 5/2015 | Boonekamp ........... A01K 63/06 |
| | | | | 315/153 |

FOREIGN PATENT DOCUMENTS

| | | | | |
|---|---|---|---|---|
| EP | 3492037 A1 | * | 6/2019 | ............. A61B 1/045 |
| JP | 2015013175 A | | 1/2015 | |

* cited by examiner

*Primary Examiner* — Mohammed A Hasan

(57)     ABSTRACT

The present disclosure relates generally to illumination devices, systems, and methods for ophthalmic surgical procedures. Certain aspects of the present disclosure provide an illumination system which monitors and determines the amount of light delivered to a tissue within the ocular space, based upon data received from an imaging system. In certain aspects, if the amount of light delivered to the tissue is determined to be excessive, the illumination system may modify at least one parameter associated with the delivered light to reduce and/or eliminate phototoxic effects thereof. In certain aspects, if the amount of light delivered to the tissue is determined to be excessive, the illumination system may alert a surgeon, who may then trigger modification of the at least one parameter associated with the delivered light to reduce and/or eliminate phototoxic effects thereof.

14 Claims, 6 Drawing Sheets

SYSTEMS AND METHODS FOR LIGHT MODULATION DURING OPHTHALMIC SURGERY

BACKGROUND

The present disclosure relates to an automated strategy for quantifying exposure of a retina to light energy during an ophthalmic procedure. Certain ophthalmic surgical procedures require high magnification and imaging of the retina and surrounding tissue within the vitreous cavity of a patient's eye. During such procedures, the retina is illuminated by bright light, which is emitted primarily by a hand-operated light pipe/endoilluminator or another suitable directed light source. Vitrectomy is a representative procedure in which such directed light is used to illuminate the vitreous cavity. As understood in the art, vitrectomy involves the precise removal of vitreous humor gel to facilitate access to and repair of a torn or separated retina, macular holes, or diseased/damaged ocular tissue. Cataract surgery and other ophthalmic procedures likewise use internally and/or externally directed light for the purpose of illumination and imaging.

The retina, which is a thin, highly delicate lining situated on posterior internal surfaces of the eyeball, acts as an appendage of the brain. That is, sensory neurons, intricate neural circuits, and synaptic connections of the retina respond to incident light with corresponding nerve impulses, which are ultimately transmitted to the brainstem via the optic nerve. Due to photosensitivity of the delicate retina tissue, directed light energy falling incident on the retina surface poses a risk of light toxicity, with this risk being highly variable and factor-dependent.

Currently, light output during ophthalmic procedures is characterized relative to a model using worst-case assumptions. Due the wide variation between surgical lighting techniques of individual surgeons, differences in lighting technology, and the length of surgery, predictions made using worst-case models seldom coincide with actual light toxicity risk or exposure. As a result, a surgeon may be distracted during surgery by overaggressive light toxicity notifications and false alarms.

Anatomically, the eye is divided into two distinct regions—the anterior segment and the posterior segment. The anterior segment includes the lens and extends from the outermost layer of the cornea (the corneal endothelium) to the posterior lens capsule. The aqueous humor fills the space between the lens and the cornea and helps maintain intraocular pressure. The posterior segment includes the portion of the eye behind the lens capsule. The posterior segment extends from the anterior hyaloid face to the retina, with which the posterior hyaloid face of the vitreous body is in direct contact. The posterior segment is much larger than the anterior segment.

The posterior segment includes the vitreous body—a clear, colorless, gel-like substance that makes up two-thirds of the eye's volume, giving it form and shape before birth. It is composed of approximately 1% collagen and sodium hyaluronate and 99% water. The anterior boundary of the vitreous body is the anterior hyaloid face, which touches the posterior capsule of the lens, while the posterior hyaloid face forms its posterior boundary, and is in contact with the retina. The vitreous body is not free-flowing like the aqueous humor and has normal anatomic attachment sites. One of these sites is the vitreous base, which is a 3-4 mm (millimeter) wide band that overlies the or a serrata. The optic nerve head, macula lutea, and vascular arcade are also sites of attachment. The vitreous body's major functions are to hold the retina in place, maintain the integrity and shape of the globe, absorb shock due to movement, and to give support for the lens posteriorly. In contrast to aqueous humor, the vitreous body is not continuously replaced. In a process known as vitreous syneresis, the collagen of the vitreous body may break down and result in retinal detachment.

Vitrectomy and other vitreoretinal surgical procedures are commonly performed in the posterior segment of the eye and are utilized to treat many serious conditions of the posterior segment. For example, vitreoretinal surgical procedures are performed to treat conditions such as age-related macular degeneration (AMD), diabetic retinopathy (DR), diabetic vitreous hemorrhages, macular holes, retinal detachments, epiretinal membrane, cytomegalovirus (CMV) retinitis, and many other ophthalmic conditions.

An ophthalmic surgeon typically performs vitreoretinal procedures with a microscope or other viewing system that provides a clear and magnified image of the posterior segment. Several small incisions, about 1 mm in length, are made on the sclera at the pars plana. The surgeon then inserts microsurgical instruments through the incisions, such as an infusion line to maintain the pressure and shape of the eye during surgery, and instruments to cut or ablate and remove the vitreous body. Often, an endoilluminator containing a small optical fiber is inserted into the eye to provide illumination, which is generated by a light source, such as a xenon lamp or LED (light emitting diode) source, and carried into the eye by the optical fiber.

During such procedures, proper illumination of the inside of the eye is important. However, excessive and/or intense illumination may cause light-induced damage to the retina, and in particular, the photoreceptors and retinal pigment epithelium (RPE). For example, the wavelengths of light used for illumination, the power of the light source, the intensity of light, e.g., due to close proximity of the endoilluminator to the retina, and the cumulative light delivered (CDL) may all contribute to a phototoxic effect on the retina.

Accordingly, what is needed in the art are improved illumination systems for reducing light-induced damage to the eye during ophthalmic surgical procedures.

SUMMARY

Disclosed herein are automated light toxicity prevention methods and systems for accurately quantifying exposure of a patient retina to directed light energy during an ophthalmic procedure. The toxic potential of light energy during such a procedure widely varies based on a number of factors, including the linear distance between the retina and the light source, the exposed surface area of the retina, length of time that the area is exposed to light energy, and the spectral content and intensity of the light energy. By measuring working images of the retina during the procedure and quantifying light energy distribution in terms of cumulative energy spectral density, a more accurate assessment of true light energy exposure and attendant toxicity risk is afforded to the surgeon. This in turn allows the surgeon or any other attending clinician to make more informed decisions regarding retina illumination. Benefits of the present teachings include the potential use of higher intensity light and/or application of light of a different spectral content, perhaps for a longer duration before a light toxicity hazard warning manifests itself. Once a light toxicity hazard is indicated, an appropriate warning or notification is issued, along with possible adjustment of control settings of the light source in some embodiments.

In an exemplary embodiment, a system for quantifying light exposure of a patient retina during an ophthalmic procedure includes a light source, a camera, an indicator device, and an electronic control unit (ECU). The light source is configured to illuminate the patient retina with directed light during the ophthalmic procedure to thereby produce an illuminated retina surface. As this occurs, the camera collects digital or analog image data of the illuminated retina surface. The ECU, which is in communication with the camera, receives the image data and thereafter calculates a cumulative spectral energy density of the directed light energy falling incident upon the retina. The ECU then displays incident light energy information via the above-noted indicator device, itself having multiple possible configurations as described herein. In another embodiment, the ECU may be in communication with the light source, and may proceed to execute a control action relative to the light source based on assessment of possible light toxicity.

As used herein, the term "cumulative energy spectral density" refers to the energy density of incident light, integrated over time and spread across different wavelengths, i.e., the cumulative exposure of the retina to light energy in particular bandwidths of the electromagnetic spectrum, and to associated frequencies and intensities of such light. The control action is executed in response to the cumulative energy spectral density of delivered/incident light exceeding a light toxicity threshold, which may be a preset value determined by the user/surgeon or based on a calibration, and includes activating the indicator device.

The ECU as described herein integrates an energy level of the directed light over the course of the ophthalmic procedure, commencing with the onset of illumination of the retina. In other words, integration is not triggered when the light source is turned on, but rather when active illumination of the retina commences, i.e., when light energy falls incident upon the retina.

The ECU may optionally determine the above-noted cumulative energy spectral density as multiple different cumulative densities to provide a higher level of precision. For one example, the ECU may calculate cumulative light energy based on multiple light sources, such as a light pipe/probe and a chandelier. In another example, the ECU may calculate the cumulative density for multiple different areas or zones of the illuminated retina surface. In such an embodiment, the ECU is able to execute the control action in response to the cumulative energy spectral density of any one of the zones exceeding a light toxicity threshold, which itself may be several zone-specific thresholds to account for potential differences in light sensitivity across the exposed area of the retina.

The indicator device contemplated herein includes a display screen in certain embodiments. The ECU automatically presents a light energy distribution pattern or "heat map" of the illuminated retina surface to the surgeon via the display screen. The heat map is thus representative of the distribution of the cumulative energy spectral density, thereby pinpointing locations of relatively high or low energy concentrations, as delivered to the retina. A fundus image may be used as an optional backdrop to such a heat map, i.e., the heat map could be presented as an overlay or displayed on top of the fundus image to accurately indicate zones corresponding to local "hot spots", such as areas exposed to a disproportionately high amount of incident light energy. Optional approaches include altering overlay colors in a manner similar to adding yellow highlighter to parts of the displayed image that exceed a threshold.

In some aspects of the present disclosure, the ECU may be configured to automatically adjust control settings of the light source in response to exceeding the light toxicity threshold(s). For example, a wavelength and/or an intensity of the directed light may be modified as needed without manual intervention by the surgeon. The control action in such an embodiment may include automatically adjusting the wavelength and/or intensity in real-time via the ECU.

A method is also disclosed for quantifying light energy exposure of a patient retina during an ophthalmic procedure. An embodiment of the method includes illuminating the patient retina with directed light from a light source during the ophthalmic procedure to thereby produce an illuminated retina surface, and collecting image data of the illuminated retina surface using a camera. The method also includes receiving the image data from the camera via an ECU, and then calculating a cumulative energy spectral density, via the ECU, of the directed light energy falling incident upon the retina during the ophthalmic procedure. In response to the cumulative energy spectral density exceeding a light toxicity threshold, the method includes executing a control action via the ECU, wherein the control action is indicative of possible light toxicity, the control action including activating an indicator device.

The ECU in a possible embodiment includes a processor, input/output (I/O) circuitry in communication with the processor and with a light source, an indicator device, a camera, and memory. On the memory is recorded computer-readable instructions, the execution of which by the processor causes the ECU to receive collected image data from the camera during the ophthalmic procedure. The collected image data depicts the illuminated retina surface. Execution of the instructions also causes the ECU to calculate a cumulative energy spectral density of the directed light energy falling incident upon the retina during the ophthalmic procedure, and to execute a control action indicative of possible light toxicity in response to the cumulative energy spectral density exceeding a light toxicity threshold, including activating the indicator device. The threshold may be an arbitrary value set by the surgeon, based on experience with previous surgeries and the surgeon's medical judgement. Alternatively, the threshold may be based upon a calibration process which quantifies an appropriate safety threshold.

According to certain embodiments, an illumination system is provided. The illumination system comprises: a light source configured to generate a light beam for illuminating an ocular space, the light source comprising: a light driver in data communication with a system controller and configured to drive the light source to generate the light beam; and the system controller, comprising: a memory comprising executable instructions; and a processor in data communication with the memory and configured to execute the instructions to cause the illumination system to: determine an amount of light delivered to a tissue within the ocular space, the determination at least partially based on data received from an imaging system associated with the system controller and light source; and modify with the light driver, based on the determined amount of light delivered to the tissue within the ocular space, at least one parameter associated with the light beam generated by the light source.

The above-described features and advantages and other possible features and advantages of the present disclosure will be apparent from the following detailed description of the best modes for carrying out the disclosure when taken in connection with the accompanying drawings.

Figure 1:
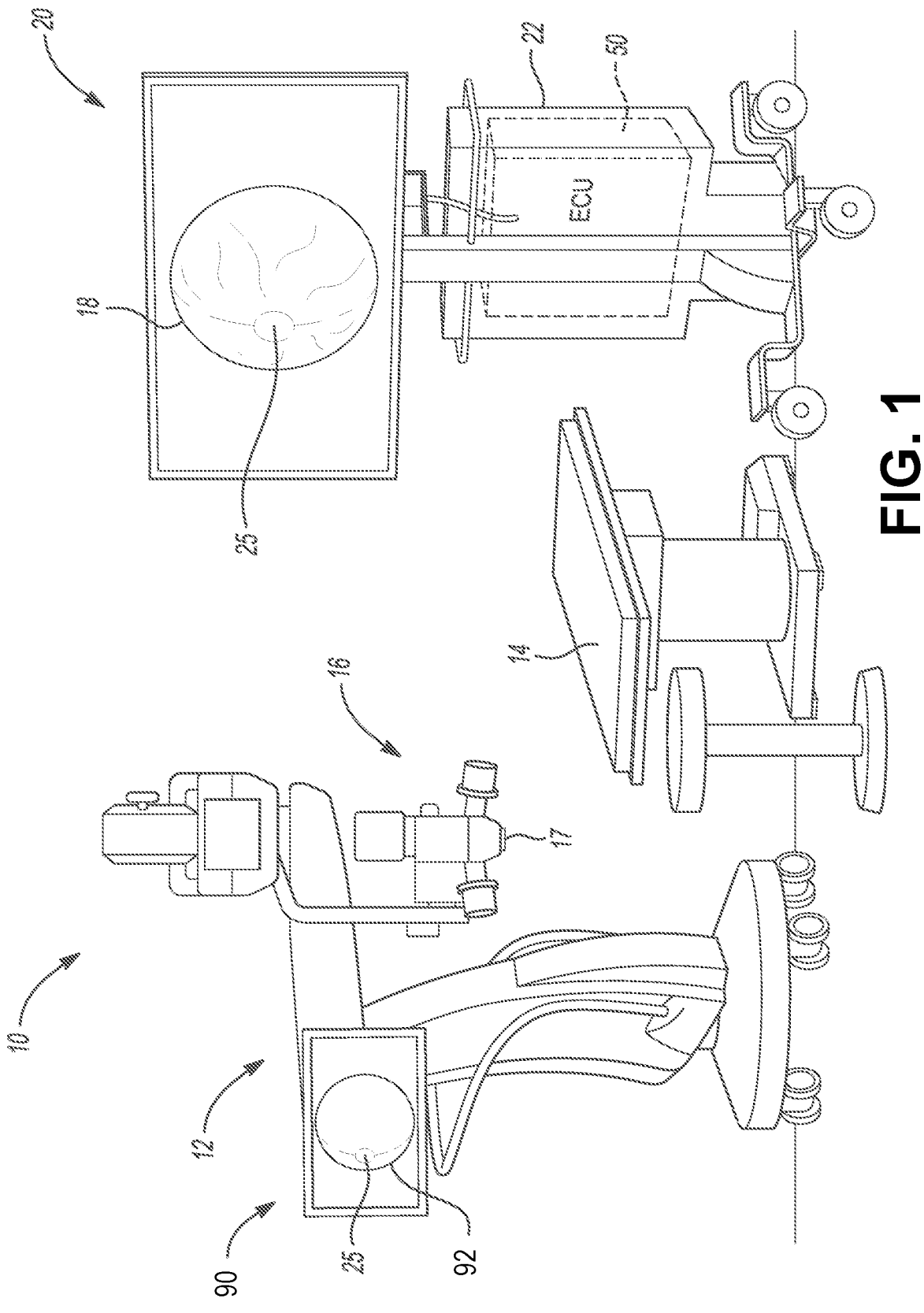
FIG. 1 is a schematic illustration of an operating room setup using an automated system for quantifying light exposure for preventing a possible light toxicity or exposure condition during a representative ophthalmic procedure.

The foregoing and other features of the present disclosure are more fully apparent from the following description and appended claims, taken in conjunction with the accompanying drawings.

DETAILED DESCRIPTION

Embodiments of the present disclosure are described herein. It is to be understood, however, that the disclosed embodiments are merely examples and other embodiments can take various and alternative forms. The figures are not necessarily to scale. Some features could be exaggerated or minimized to show details of particular components. Therefore, specific structural and functional details disclosed herein are not to be interpreted as limiting, but merely as a representative basis for teaching one skilled in the art to variously employ the present disclosure. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Certain terminology may be used in the following description for the purpose of reference only, and thus are not intended to be limiting. For example, terms such as "above" and "below" refer to directions in the drawings to which reference is made. Terms such as "front," "back," "fore," "aft," "left," "right," "rear," and "side" describe the orientation and/or location of portions of the components or elements within a consistent but arbitrary frame of reference which is made clear by reference to the text and the associated drawings describing the components or elements under discussion. Moreover, terms such as "first," "second," "third," and so on may be used to describe separate components. Such terminology may include the words specifically mentioned above, derivatives thereof, and words of similar import.

Referring to the drawings, wherein like reference numbers refer to like components, a representative ophthalmic surgical suite 10 is depicted schematically in FIG. 1. As appreciated by those skilled in the art, such a surgical suite 10 may be equipped with a multi-axis surgical robot 12 and an operating table 14. When the surgical suite 10 is used for performing a representative vitreoretinal surgery or other surgical or diagnostic procedure, the surgical robot 12 is connected to an ophthalmic microscope 16 through which a surgeon is able to view a patient's ocular anatomy under high magnification. Using associated hardware and software, the surgeon is able to view highly magnified images 18 and 92, e.g., of a retina 25 thereof, which may be achieved via corresponding high-resolution medical display screens 20 and 90.

Also present within the exemplary surgical suite 10 of FIG. 1 is a cabinet 22 containing an electronic control unit (ECU) 50, with an exemplary embodiment of the ECU 50 depicted in FIG. 2 and described in detail below. The cabinet 22, which is shown collocated with the display screen 20, may be positioned elsewhere in the suite 10 in other embodiments. Such a cabinet 22, which may be constructed of a lightweight and easily sanitized construction, e.g., painted aluminum or stainless steel, is used to house the ECU 50 and protect its constituent hardware from possible ingress of dust, debris, and moisture.

Within the scope of the disclosure, the vitreoretinal surgical procedure performed within the surgical suite 10 involves the use of directed task lighting for illumination of the retina 25. Such light is primarily emitted by a light source 32 as shown in FIG. 2, with additional lighting provided by an external lamp 17 mounted to the ophthalmic microscope 16. Over time, and based on a host of variable factors, the use of such light can pose a light toxicity risk affecting the photosensitivity functions of the retina 25. In order to mitigate such risk, the ECU 50 of the present disclosure is configured to automatically quantify light energy exposure of the retina 25, with an end goal of transmitting accurately derived alarms or warning to the attending surgeon. The ECU 50 may also perform optional exposure-reducing active control actions as set forth below.

Figures 2, 3:
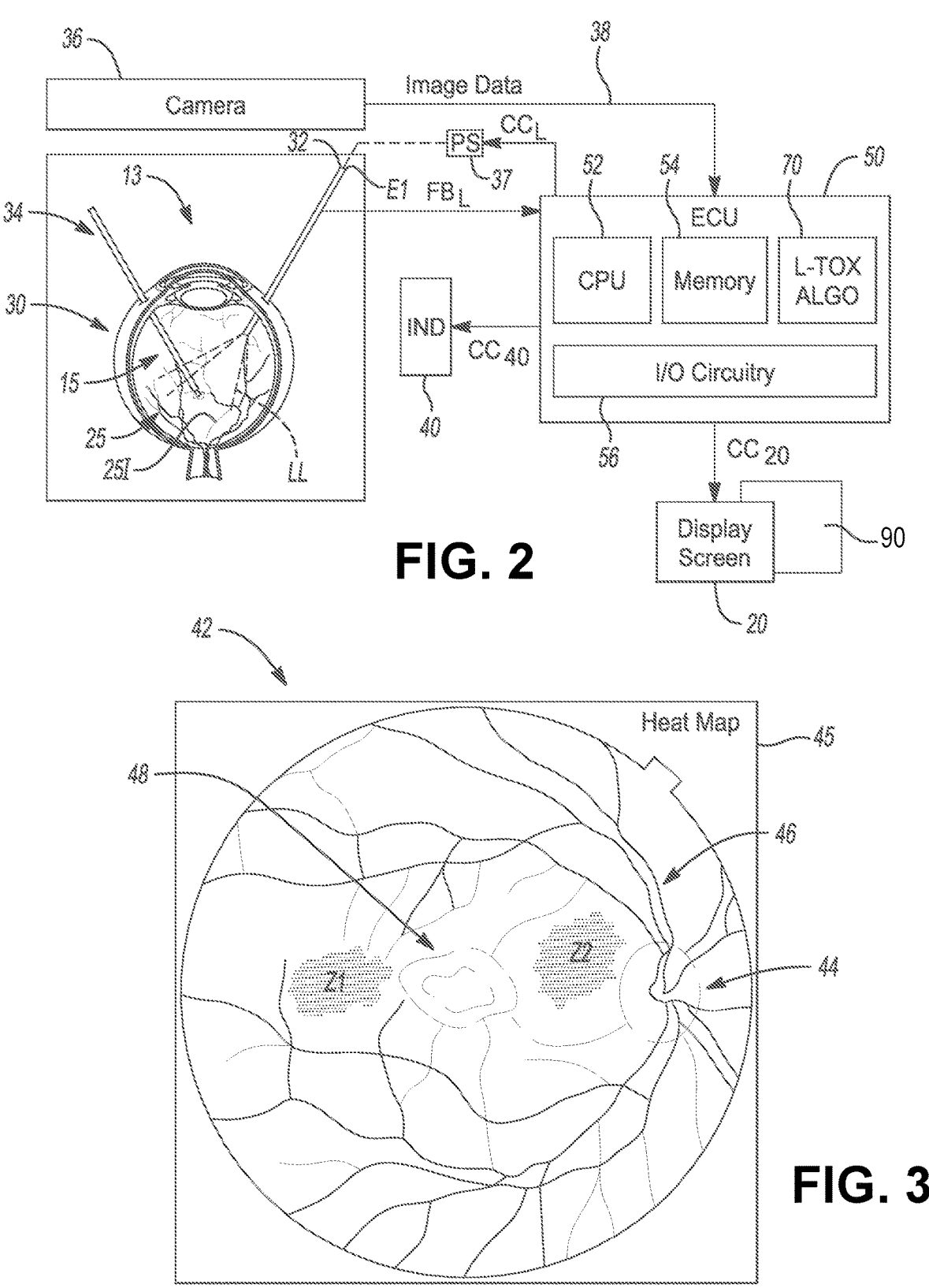
FIG. 2 is a schematic depiction of an embodiment of the automated system shown in FIG. 1.
FIG. 3 is a schematic illustration of exemplary fundus image-based heat map in accordance with an aspect of the disclosure.

Referring to FIG. 2, a representative patient eye 30 is shown undergoing an ophthalmic procedure 13, in this instance an invasive vitreoretinal surgery. During the course of an ophthalmic procedure 13 of this type, the light source 32 noted above is inserted into a vitreous cavity 15 of the patient eye 30. Light LL emitted from the light source 32, as well as some light from the microscope lamp 17 of FIG. 1, falls within a predetermined range of wavelengths depending on the illumination task. The light source 32 may be embodied as a light pipe or an endoilluminator in some embodiments, possibly with a controllable intensity and/or spectral content, i.e., the particular wavelengths and associated colors of light within the electromagnetic spectrum. Exemplary applications may be envisioned in which a surgeon desires a blue light shift for improved visibility, with the source light 32 possibly constructed to adjust its output spectrum in response to commands from the surgeon. Various lighting technologies may be used to emit the light LL, such as but not limited to red/green/blue (RGB) lasers, light-emitting diodes (LEDs), halogen bulbs, etc.

During the ophthalmic procedure 13, the surgeon may also insert a surgical tool 34 into the vitreous cavity 15 in order to perform a given operating task on or in proximity to the retina 25. Non-limiting exemplary embodiments of the surgical tool 34 include devices as forceps, extrusion hand pieces, bladed vitrectomy probes, scissors, illuminated or non-illuminated laser probes, and/or infusion tools. With respect to the light source 32, the directed light LL is emitted from a distal end E1 thereof, where the directed light LL falls incident upon exposed surfaces of the retina 25 to produce an illuminated retina surface 25I. The light source 32 is coupled to an accompanying filtered power supply (PS) 37, such as a filtered wall outlet or a battery pack and power inverter suitable for ensuring reliable generation and transmission of the directed light (arrow LL).

Figure 4:
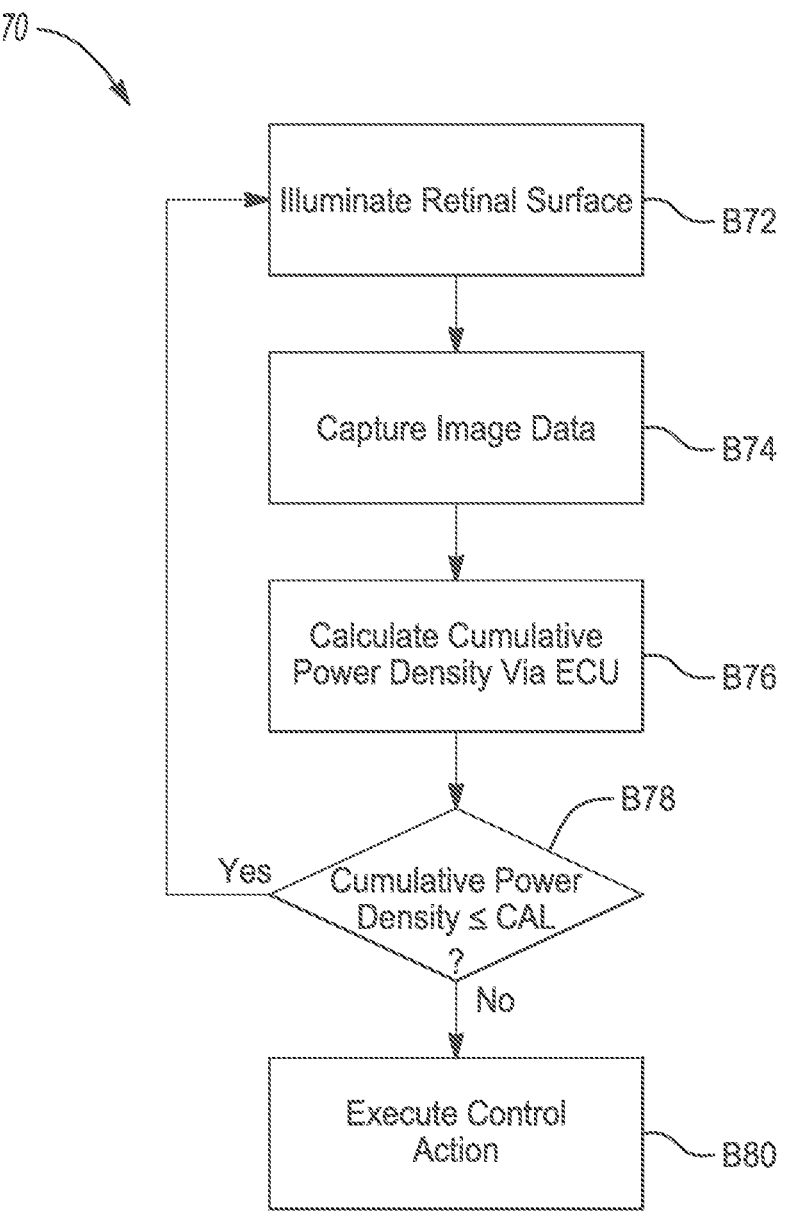
FIG. 4 is a flow chart describing an exemplary method for quantifying light energy exposure using the automated system shown in FIG. 1.

During the course of the ophthalmic procedure 13, a digital or analog camera 36 or another high-resolution medical imaging device collects image data 38 of the illuminated retina surface 25I, and thereafter transmits the collected image data 38 to the ECU 50 for processing in accordance with a light toxicity algorithm (L-TOX ALGO) 70. A method enabled by the algorithm 70 is depicted in FIG. 4 and described in detail below. An indicator device (IND) 40 is likewise in communication with the ECU 50, and is configured to activate/turn on in response to an indicator control signal (arrow $CC_{40}$) from the ECU 50. In response to the indicator control signal (arrow $CC_{40}$), and depending on the particular configuration of the indicator device 40, the indicator device 40 may provide a suitable audible, visible, and/or tactile alarm or warning.

For instance, the indicator device 40 may be embodied as a speaker, in which case the indicator control signal (arrow $CC_{40}$) may cause the indicator device 40 to sound an audible tone. Alternatively, the indicator device 40 may include a color-coded lamp, such that receipt of the indicator control signal (arrow $CC_{40}$) causes the indicator device 40 to light up in a readily identifiable manner, e.g., using red light. In either embodiment, the ECU 50 could also use the display screen 20 and/or 90 as part of the indicator device 40 to present an intuitive graphical depiction of light energy concentrations or distribution patterns on the illuminated retina surface 25I.

Within the scope of the present disclosure, the rate of light toxicity alarms is reduced relative to conventional approaches operating on a modeled worst-case scenario of the type described above. Instead, the ECU 50 in some embodiments is configured to receive light output data (arrow $F_{BL}$) as electronic feedback signals from the light source 32 that are indicative of the intensity, wavelength, temperature, and/or other relevant output parameters. The ECU 50 in such embodiments thereafter quantifies the actual distribution and energy spectral density of the directed light LL from the light source 32 across the illuminated retina surface 25I.

Still referring to FIG. 2, the ECU 50 is configured to receive the collected image data 38 from the camera 36 in real-time during the ophthalmic procedure 13, with the received collected image data 38 depicting the illuminated retina surface 25I and describing corresponding light intensity levels for each constituent image pixel. The ECU 50 estimates or calculates a cumulative energy spectral density of the directed light LL falling incident upon the retina 25 during the course of the ophthalmic procedure 13, with the ECU 50 doing so using the digital image data 38 and possibly the light output data (arrow $F_{BL}$) in different embodiments. As noted above, the term "cumulative energy spectral density" as used herein considers light energy density across different wavelengths of the electromagnetic spectrum, i.e., in particular wavelength ranges associated with light toxicity risk. The ECU 50 thereafter executes an appropriate control action indicative of possible light toxicity relative to one or more corresponding light toxicity thresholds.

Although the ECU 50 is depicted schematically as a unitary box for illustrative clarity and simplicity, the ECU 50 could include one or more networked devices each with a central processing unit (CPU) or other processor 52 and sufficient amounts of memory 54, including a non-transitory (e.g., tangible) medium that participates in providing data/instructions that may be read by the CPU 52. Instructions embodying the algorithm 70 may be stored in memory 54 and executed by the CPU 52 to perform the various functions described herein, thus enabling the present method. The memory 54 may take many forms, including but not limited to non-volatile media and volatile media.

As will be appreciated, non-volatile media may include optical and/or magnetic disks or other persistent memory, while volatile media may include dynamic random-access memory (DRAM), static RAM (SRAM), etc., any or all of which may constitute a main memory of the ECU 50. Input/output (I/O) circuitry 56 may be used to facilitate connection to and communication with the various peripheral devices used during the ophthalmic procedure 13, inclusive of the camera 36, the light source 32, the indicator device 40, and the display screen(s) 20 and/or 90. Other hardware not depicted but commonly used in the art may be included as part of the ECU 50, including but not limited to a local oscillator or high-speed clock, signal buffers, filters, etc.

Within the scope of the disclosure, the ECU 50 is programmed in software, equipped in hardware, and thus configured to integrate a power level over time of the directed light LL falling incident upon the retina 25 over the duration of the ophthalmic procedure 13. In this manner the ECU 50 derives the above-noted cumulative energy spectral density. That is, rather than considering the full duration over which the light source 32 is turned on, i.e., without respect to whether the directed light LL from the light source 32 actually illuminates any portion of the retina 25, the ECU 50 instead evaluates distribution and concentration of spectral energy from the distributed light LL on the retina 25 in more meaningful terms, e.g., in watts per minute, watts per hour, etc., possibly distinguishing between different zones of the retina 25.

Referring briefly to FIG. 3, the retina 25 of FIG. 2 is shown as a representative fundus image 42. As appreciated in the art, a fundus image is a color, black and white, or grayscale image of various key structure of the retina 25, primarily the optic disc 44, the retinal artery 46 and surrounding veins stemming therefrom, and the macula 48. The fundus image 42, being ubiquitous in ophthalmic practice and thus familiar, may be used as a backdrop to a displayed heat map 45. In such a configuration, the ECU 50 may be configured to digitally divide or otherwise separate the illuminated retina surface 25I into multiple virtual zones, and to map the cumulative energy spectral density to the illuminated retina surface 25I, such that each one of the multiple zones has a corresponding cumulative energy spectral density.

In such a configuration, the ECU 50 could optionally overlay the heat map 45 onto the fundus image 42 during the ophthalmic procedure 13 of FIG. 2, with this information presented in real-time via the display screen 20 and/or 90 of FIG. 1. The heat map 45 thus intuitively provides information that, at a glance, is indicative of a distribution or concentration of the cumulative energy spectral density across the illuminated retina surface 25I shown in FIG. 2. Such an approach provides a greater level of granularity or localized precision relative to treating the entire retina 25 as having equal light sensitivity, or as receiving equal exposure to the directed light LL of FIG. 2.

In the course of performing the representative ophthalmic procedure 13 of FIG. 2, a surgeon may be expected to move the distal end E1 around the vitreous cavity 15. As a result, the total exposed surface area of the retina 25 is likely to be illuminated unequally, and to a degree that is largely dependent on the location/distance and orientation of the distal end E1 relative to the retina 25, as well as on the intensity and other toxicity-relevant spectral content of the directed light LL. As a result, zones of the illuminated retina surface 25I of FIG. 2 may receive a greater density or concentration of the directed light LL relative to other zones, such as when the surgeon lingers in particular area of the retina 25 when performing an intricate surgical repair. From a qualitative standpoint, therefore, zones receiving a greater accumulated light energy density may be considered by the ECU 50 to be localized "hot spots". Two such zones are represented schematically in FIG. 3 as zones Z1 and Z2, with zones Z1 and Z2 depicted as flanking the macula 48 solely for the purposes of illustration.

The ECU 50 of the present disclosure is equipped to handle such disparity by integrating power both spatially, i.e., across the surface area of the retina 25, and temporally, i.e., with respect to the duration of exposure. The ECU 50 then executes a suitable control action in response to the cumulative energy spectral density of at least one of the multiple different zones Z1 and/or Z2, or of the entire illuminated retina surface 25I, exceeding a corresponding light toxicity threshold. Such thresholds may be the same or zone-specific in different embodiments, as noted above, with the ECU 50 for instance using higher thresholds in zones in which tissue of the retina 25 is more resilient to light than others.

In still other embodiments, the total accumulated energy spectral density of the directed light LL falling incident on the retina 25 may be used, e.g., in watts per millimeter squared ($W/mm^2$), again possibly with different light toxicity thresholds applied to different zones of the retina 25 as noted above. For instance, zones in which photoreceptors of the retina 25 are more heavily concentrated than others may have a corresponding light toxicity threshold that is lower relative to other zones, with an effective "watts per rod" or "watts per cone" level of precision being realizable within the scope of the disclosure. Such light toxicity thresholds could be adjusted over time based on post-operative history or other factors to provide improved long-term results.

Referring now to FIG. 4, a method is made possible by execution of computer-readable instructions embodying the algorithm 70. That is, execution of instructions stored or recorded in memory (M) of the ECU 50 shown in FIG. 2 may cause the processor 52 and other hardware of the ECU 50 to perform the method. For clarity, therefore, such a method is referred to hereinafter as the method 70.

A representative embodiment of the method 70 commences with logic block B72, which includes illuminating the patient retina 25 of FIG. 2 with directed light LL from the light source 32, along with possibly some additional light from the microscope lamp 17 of FIG. 1, during the ophthalmic procedure 13, with the collective directed light LL producing the illuminated retina surface 25I. Thus, surgical steps preceding implementation of logic block B72 may include creating an incision in the eye 30, inserting a cannula, and inserting the light source 32 into the vitreous cavity 15. Once the distal end E1 of the light source 32 is present within the vitreous cavity 15 and energized by the power supply 37, the light source 32 in some embodiments initiates transmission of the light output data (arrow $FB_L$) to the ECU 50. Such light output data (arrow FBL) once again is primarily the contribution of the light source 32, but may also describe light emitted by the microscope lamp 17 in some embodiments. The method 70 then proceeds to logic block B74.

Logic block B74 of FIG. 4 may entail receiving the light output data (arrow $FB_L$) from the light source 32, the light output data being descriptive of an intensity and spectral content of directed light emitted by the light source when illuminating the patient retina. Logic block B74 also includes collecting the image data 38 of FIG. 2 using the camera 36, with the image data 38 possibly including two-dimensional or three-dimensional images of the illuminated retina surface 25I. The camera 36 may be integral with the ophthalmic microscope 16 of FIG. 1 in some embodiments, or the camera 36 may be a separate device. As the collected image data 38 is formed in digital embodiments from image pixels, logic block B74 may include accompanying quantitative information describing corresponding illumination levels of each of the constituent image pixels, including for instance the intensity thereof.

As part of logic block B74, the image data 38 is transmitted to the ECU 50 over suitable transfer conductors. Logic block B74 thus also includes receiving the collected image data 38 from the camera 36 via the ECU 50. In conjunction with the light output data (arrow $FB_L$) provided in logic block B72, the image data 38 enables the ECU 50 to estimate power, intensity, wavelengths and other relevant energy spectral content of the directed light (LL) from the light source 32, as well as the distribution thereof across the retina 25. The method 70 then proceeds to logic block B76.

At logic block B76, the ECU 50 next estimates or calculates the cumulative energy spectral density of the directed light LL falling incident on the retina 25, using the light output data (arrow $FB_L$) of logic block B72 and the image data 38 of logic block B74. Estimation may occur in embodiments that are based on the collected image data 38 alone, e.g., using models based on the brightness, color, distribution, and other factors present in the images comprising the collected image data 38. More accurate results may be enjoyed in embodiments using the light output data (arrow $FB_L$), e.g., with foreknowledge of the power of the light source 32, the spread function of the light source 32, the distance of the light source 32 from the retina 25, and the length of time the retinal tissue is exposed to the light LL.

Logic block B76 may include calculating an average or normalized energy spectral density across the entire illuminated retina surface 25I, or the ECU 50 may calculate multiple discrete energy spectral densities in a zone-specific manner. When using the latter approach, e.g., as depicted in FIG. 3, the surgeon is made aware of any disparity in light energy concentrations across the surface of the retina 25. The method proceeds to logic block B78 once the ECU 50 has calculated the cumulative energy spectral density or zone-specific energy spectral densities.

At logic block B78, the ECU 50 of FIG. 2 next compares the cumulative energy spectral density or densities to respective light toxicity thresholds. The method 70 repeats logic block B72 when none of the light toxicity thresholds have been exceeded. The method 70 proceeds in the alternative to logic block B80 when the ECU 50 determines that one or more of the light toxicity thresholds have been exceeded.

Logic block B80 involves, in response to the cumulative energy spectral density exceeding a light toxicity threshold, executing a control action via the ECU 50. As noted above, the control action is indicative of possible light toxicity, and includes activating the indicator device 40. As part of logic block B80, the ECU 50 may consider the magnitude by which a given light toxicity threshold was exceeded in logic block B78 when determining which of many possible control actions the ECU 50 should execute in a given situation. That is, the control action could be commensurate with the magnitude of a difference between the exceeded light toxicity threshold and the cumulative energy spectral density, with the ECU 50 possibly escalating the corresponding alarms as the magnitude increases.

An illustrative example includes establishing a threshold light toxicity level for representative zones Z1 and Z2 of FIG. 3. Through the course of the ophthalmic procedure 13, the ECU 50 automatically integrates power of the directed light LL, delivered over time, in different regions or zones of the illuminated retina surface 25I, including the zones Z1 and Z2. The ECU 50 could display a color-coded version of the heat map 45 of FIG. 3 via the display screens 20 and/or 90 of FIG. 1, which would enable the surgeon to discern at a glance whether particular zones are being over-irradiated relative to others. In an embodiment, the ECU 50 could modify the color of "hotter" zones as cumulative energy spectral density in that zone increases, such as by gradually coloring the zone from yellow to red. Upon crossing a given light toxicity threshold for a given zone, the ECU 50 could activate the indicator device 40 of FIG. 2, e.g., a lamp or an audible alarm tone.

Additionally, the ECU 50 within the scope of the disclosure could respond to a given threshold light toxicity level being exceeded by automatically adjusting a setting of the light source 32. Such an option could be selectable by the surgeon or selectively bypassed or overridden in other embodiments. Representative control actions in such an event may include adjusting a power level from the power supply 37 of FIG. 2 to turn down the power of the light source 32, and/or changing the wavelength and/or intensity of the directed light LL emitted by the light source 32 during the course of the ophthalmic procedure 13. The latter control action could encompass changing the spectral content thereof to reduce the ultraviolet/violet/blue light content, thereby making the energy safer for the eye, albeit at the potential expense of less detail.

By using the ECU 50 of FIGS. 1 and 2, the intuitive heat map 45 of FIG. 3, and the algorithm 70 shown in FIG. 4, a surgeon performing the ophthalmic procedure 13 shown in FIG. 2 is made aware, in a more realistic and localized manner, of the light toxicity risk attendant to directing the incident light LL from the described light source 32 onto the retina 25. Because light toxicity alarms are not triggered unless and until a given energy spectral density-specific threshold has been exceeded, the present approach should help reduce the number of false alarms relative to conventional worst-case modeling scenarios.

Moreover, reducing the rate of false alarms provides a surgeon with an increased confidence level. Alarms that do sound in the course of performing the ophthalmic procedure 13 are, in other words, very likely to be true alarms and, as a result, less likely to be silenced or disregarded without action. Embodiments may be standalone, i.e., the ECU 50 and its attendant logic may be used with an existing ophthalmic microscope 16, camera 36, and light source 32. Alternatively, any or all of the described hardware could be integrated, such that the programmed functions of the ECU 50 when executing method 70 of FIG. 4 are seamless.

Note that, as described herein, a distal end, segment, or portion of a component refers to the end, segment, or portion that is closer to a patient's body during use thereof. On the other hand, a proximal end, segment, or portion of the component refers to the end, segment, or portion that is distanced further away from the patient's body.

Although generally described with reference to ophthalmic surgical devices and systems, the devices and systems described herein may be implemented with other devices and systems, such as devices and systems for other surgeries, without departing from the scope of the present application.

As used herein, the term "about" may refer to a +/−10% variation from the nominal value. It is to be understood that such a variation can be included in any value provided herein.

The present disclosure relates generally to illumination devices and systems for surgical procedures, and more specifically, to endoillumination devices and systems for ophthalmic surgical procedures, as well as associated methods of use. In vitreoretinal surgery, a fiber optic illuminator may be used to illuminate the posterior segment of the eye to facilitate restoration of vision due to retinal detachment and other complications. However, the cumulative light delivered (e.g., in lumens), duration of illumination (e.g., vitreoretinal surgeries typically last 20-120 minutes), and intensity of light due to close proximity of a distal end of the illuminator to the retina (e.g., 6 mm on average for vitreoretinal surgeries), can be damaging to photoreceptors within the retina. Further, blue light spectra, which may be utilized by certain conventional ophthalmic illumination systems, are well documented as being more damaging to photoreceptors than other wavelengths of visible light spectra. Accordingly, aspects of the present disclosure provide an improved illumination system for eliminating or at least reducing light-induced damage to the retina during vitreoretinal and other ophthalmic procedures.

Certain aspects of the present disclosure provide an illumination system comprising a controller in data communication with a light driver of a light source. While a light beam is generated by the light source and propagated into an eye during an ophthalmic procedure (e.g., vitreoretinal surgery), the controller may be configured to determine (i.e., quantify) an amount of light delivered to a tissue (e.g., retina) within the ocular space, based upon data received from an imaging system associated with the controller. In certain aspects, if the controller determines that the amount of light delivered to the tissue is excessive, the controller may automatically modify, via the light driver, at least one parameter associated with the light beam generated by the light source. In certain aspects, if the controller determines that the amount of light delivered to the tissue is excessive, the controller may alert a surgeon that the amount of light delivered to the tissue is excessive, so that the surgeon may trigger modification of at least one parameter associated with the light beam generated by the light source. In some embodiments, the controller may automatically trigger modification of at least one parameter associated with the light beam generated by the light source. Examples of the at least one parameter include duty cycle, pulse rate, intensity, etc., of all or certain wavelengths of the light beam. By modifying the light beam, the phototoxic effects of the light beam against the tissue may be reduced, thus reducing the risk of injury to the patient's eye and improving the safety of the ophthalmic procedure.

Figure 5:
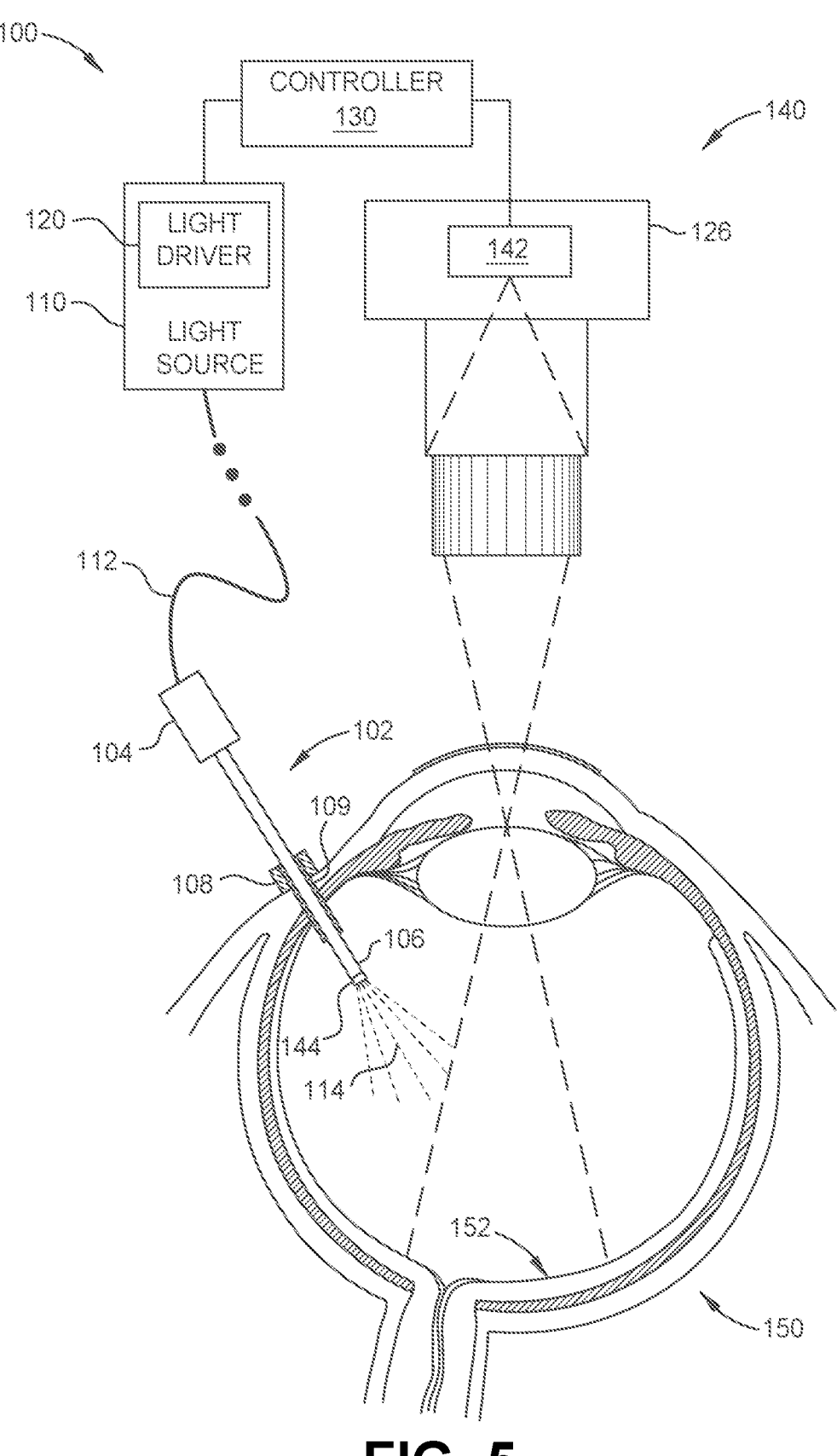
FIG. 5 illustrates an example illumination system positioned within an eye, in accordance with certain embodiments of the present disclosure.

FIG. 5 illustrates an example illumination system 100 for illuminating an ocular space of eye 150 during an ophthalmic surgical procedure, according to certain embodiments of the present disclosure. Illumination system 100 generally includes light source (e.g., light engine) 110, light driver 120, and controller 130. Light source 110 includes any suitable type of illumination light source for ophthalmic surgical procedures, such as vitreoretinal procedures. Accordingly, light source 110 may be configured to generate an appropriate illumination light, depicted as light beams 114 in FIG. 5, for illuminating a posterior segment of eye 150, including retina 152. In certain embodiments, light source 110 is a light emitting diode (LED)-based light source, such as a red-green-blue (RGB) LED source or a superluminescent diode (SLED) light source. However, other types of light sources are further contemplated, such a xenon- or halogen-based light sources, UV (ultraviolet) light sources, white light sources, etc. In certain embodiments, light source 110 is part of an illumination module within a surgical console, and in other embodiments, light source 110 is a standalone light engine. In still other embodiments, light source 110 is disposed within a handpiece of an endoilluminator, such as handpiece 104 of endoilluminator 102, described in further detail below. For example, in certain embodiments, handpiece 104 contains light source 110 within a housing or structure of handpiece 104.

As shown in FIG. 5, light source 110 further includes light driver 120, which drives light source 110 to generate light beams 114 according to input (e.g., control signals) received from controller 130, which is in data communication with light source 110 and/or light driver 120. For example, light driver 120 may include an electronic power adjustment device that provides power conversion, load, regulation, and downstream protection for light source 110. Although depicted as a component of light source 110, light driver 120 may, in certain embodiments, be a separate or distinct device or component from light source 110. In certain embodiments, light driver 120 is configured to drive light source 110 to generate, and thereafter modulate or modify, light beams 114 according to control signals received from controller 130. Example parameters of light beams 114 which may be modulated include intensity, waveform, frequency, pulse rate, pulse repetition frequency (PRF), etc., of all or certain wavelengths of light beams 114 generated by light source 110. Modulation of the one or more parameters of light beams 114 during an ophthalmic surgical procedure may facilitate reduction of the cumulative light delivered to eye 150 and/or minimization of harmful spectra of light beams 114, thereby reducing the risk of light-induced injury to eye 150, and in particular retina 152.

Controller 130 is configured to determine (e.g., quantify) an amount of light delivered to eye 150, tissues thereof (e.g., retina 152), or regions of tissues thereof (e.g., the macula of retina 152), whether such amount of light is excessive, and further cause light driver 120 to perform one or more tasks for driving light source 110, which may be in response to determining whether such amount of light is excessive. In certain embodiments, controller 130 is in data communication with viewing device 140. In certain embodiments, viewing device 140 is configured to provide a magnified, digitally optimized view of the ocular space of eye 150. Examples of suitable viewing devices 140 which may be utilized with the present disclosure include three-dimensional (3D) digital viewing systems, such as the NGENUITY® 3D Visualization System available from Alcon, Fort Worth, TX. In certain embodiments, viewing device 140 includes imaging sensor 142 in data communication with an image processor for detecting light beams 114 emitted within eye 150. Examples of suitable imaging sensors include charge-coupled device (CCD) sensors and active-pixel sensors (APS), such as a complementary metal-oxide-semiconductor (CMOS) sensors. Accordingly, controller 130 may receive imaging data associated with emitted light beams 114 from viewing device 140, either continuously or periodically, and utilize the imaging data for determining the amount of light delivered to eye 150, and whether such amount of light is excessive. For example, controller 130 may analyze the imaging data via artificial intelligence processes.

In certain embodiments, as shown in FIG. 5, endoilluminator 102 may include imaging sensor 144, which may be similar to imaging sensor 142 described above. In such embodiments, imaging data may be received by controller 130 from imaging sensor 144, in addition to or alternatively to imaging sensor 142, for determining the amount of light delivered to eye 150, and whether such amount of light is excessive.

In certain embodiments, upon determining that the amount of light delivered to eye 150 is excessive, controller 130 may be configured to provide an alert to a user, e.g., an ophthalmic surgeon, advising that the amount of light delivered to eye 150 is excessive. In certain embodiments, the alert may include or be accompanied by a number of predetermined options for modifying one or more parameters of light beams 114 to reduce phototoxicity thereof, according to predetermined settings associated with light source 110 and corresponding with desired modified parameters of light beams 114. The alert may be in the form of an audible alert, visual alert, and/or a tactile alert. For example, in certain embodiments, the alert may be displayed on a display device for viewing by the surgeon, such as a display device associated with viewing device 140, controller 130, or a surgical console, or a head-mounted display or holographic goggles worn by the surgeon. In certain embodiments, the alert may include an audible alert sounded by the surgical console. Based upon the alert, the surgeon may then trigger (e.g., through a foot pedal, pressing of an on-screen or analog button, etc.) controller 130 to cause light driver 120 to modify the one or more parameters of light beams 114, for example, according to the one or more settings associated with light source 110. The one or more settings may be predetermined (e.g., defined or preset) and/or specific to circumstances in which the amount of light delivered is determined to be excessive. In certain embodiments, the modified parameters of light beams 114 may correspond to a state of reduced phototoxicity of light beams 114, which may be visually imperceptible to the surgeon.

In certain other embodiments, upon determining that the amount of light delivered to eye 150 is excessive, controller 130 may be configured automatically to cause light driver 120 to modify the one or more parameters of light beams 114 generated by light source 110, for example, according to the predetermined settings. Accordingly, in such embodiments, no input from the surgeon is necessary, and any changes to the light beams 114 may be visually imperceptible to the surgeon.

In certain embodiments, controller 130 is integrated within a surgical console, such as a vitreoretinal surgical console, wherein controller 130 includes or refers to one or more processors and/or memory devices integrated within the surgical console. In certain other embodiments, controller 130 is a stand-alone device or module that is in wireless or wired communication with, e.g., a surgical console, light source 110, and/or light driver 120 and other devices within an operating environment. In certain embodiments, controller 130 refers to a set of software instructions that a processor associated with a surgical console is configured to execute. In certain aspects, operations of controller 130 may be executed partly by the processor associated with controller 130 and/or the surgical console and partly in a public or private cloud.

Also shown in FIG. 5 is endoilluminator 102 inserted into eye 150, which may be utilized with illumination system 100 to direct light generated by light source 110 into eye 150. Endoilluminator 102 includes handpiece 104 coupled to the proximal end of shaft or "tube" 106. Handpiece 104 is configured to provide the surgeon with a graspable portion of endoilluminator 102 to facilitate a means for manipulating the depth and location of tube 106 within eye 150, and for directing emitted light beams 114. Tube 106 is a substantially hollow metal alloy shaft (e.g., stainless steel or nitinol) or hypodermic tubing, configured to be inserted into eye 150 via an insertion cannula 108 placed through a sclerotomy 109, or small incision through the sclera of eye 150.

In certain embodiments, tube 106 is fixedly coupled to handpiece 104 such that the surgeon can rotate tube 106 by rotating handpiece 104 to adjust the incidence of light beams 114, e.g., on retina 152. In certain other embodiments, tube 106 is rotatable relative to handpiece 104. Although tube 106 of FIG. 5 is illustrated as a straight shaft, other embodiments include tube 106 having other morphologies. For example, all or a portion of tube 106 may be curved to provide light to regions of the eye that would be difficult to illuminate with a straight tube 106. In such embodiments, curved portions of tube 106 may be formed of a superelastic or shape memory alloy, such as nitinol. In certain embodiments, endoilluminator 102 and its components are an instrument kit for use in ophthalmic surgery.

Endoilluminator 102 is further configured to house one or more optical fibers which transport light beams 114 generated by light source 110 through optical cable 112, into endoilluminator 102, and out of a distal end of tube 106. In particular, a hollow portion of the tube 106 includes an interior compartment configured to house the optical fiber(s). The optical fibers may include an optical fiber array (e.g., a plurality of optical fibers in regular linear arrangement or 2-dimensional pattern arrangement) and/or a single- or multi-core optical fiber (e.g., a single-mode (SM) or multi-mode (MM) fiber with multiple cores). Generally, the optical fibers may include any type of fiber suitable for transmission of light.

Figure 6:
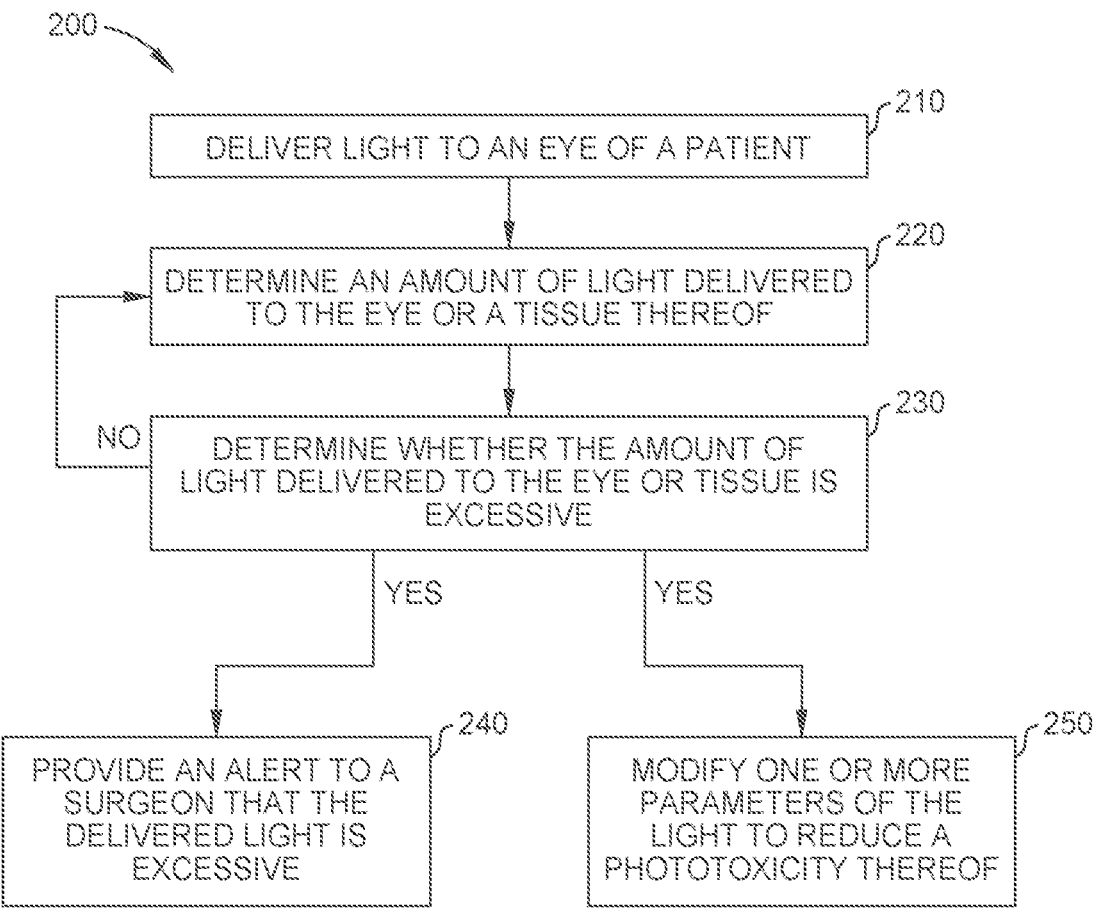
FIG. 6 illustrates a flow diagram of a method for using an illumination system, such as the illumination system of FIG. 5, in accordance with certain embodiments of the present disclosure.

FIG. 6 illustrates a flow diagram of a method 200 for using an illumination system, such as illumination system 100 of FIG. 5, in accordance with certain embodiments of the present disclosure. Method 200 may be utilized during an ophthalmic surgical procedure to reduce light-induced damage to the eye, and more particularly, the retina, which may be caused by conventional illumination systems providing excessive light thereto.

Method 200 begins at operation 210, where illumination light is generated and propagated to an ocular space of eye 150 for viewing of eye 150 with, e.g., viewing device 140. At 210, controller 130 sends a control signal to light driver 120, which causes light driver 120 to drive light source 110 to produce light beams 114. Light beams 114 may then be propagated to the eye 150 via one or more optical fibers optically coupled to light source 110 and extending through, e.g., endoilluminator 102 inserted in eye 150.

At 220, which may be performed concurrently with operation 210, controller 130 determines an amount of light delivered to eye 150, a tissue of eye 150 (e.g., retina 152), or a region of a tissue of eye 150 (e.g., the macula of retina 152). In certain embodiments, controller 130 may continuously or periodically monitor light beams 114 emitted from, e.g., endoilluminator 102, to determine the amount of light delivered to eye 150. In certain embodiments, controller 130 may continuously or periodically monitor light beams 114 reflected back from, e.g., retina 152, to determine the amount of light delivered to eye 150. For example, in certain embodiments, controller 130 may be in data communication with imaging sensor 142 of viewing device 140 and/or imaging sensor 144 disposed on a distal end of endoilluminator 102, both of which may provide controller 130 with imaging data associated with emitted or reflected light beams 114 for determination of the amount of light delivered to eye 150. In embodiments where light beams 114 are pulsed light beams, imaging sensor 142 and/or 144 may have a frame rate set to equal the pulse rate of light beams 114, or vice-versa, to facilitate image capture of the eye 150. By coordinating the pulse rate of pulsed light beams 114 with the frame rate of imaging sensor 142, the total amount of light delivered to eye 150 may be reduced in a visually imperceptible manner to the user as compared to utilizing a continuous illumination light, since imaging sensor 142 and/or 144 will only capture images of eye 150 during pulses of light beams 114.

In certain embodiments, controller 130 determines a cumulative delivered light (CDL) at 220. In certain other embodiments, controller 130 determines a macular cumulative delivered light (mCDL) at 220. In certain embodiments, the amount of light delivered to eye 150 is determined based on an intensity of light beams 114 emitted by endoilluminator 102 (e.g., over a duration of time) and/or an intensity of light beams 114 as reflected back to, e.g., imaging sensor 142 and/or imaging sensor 144 (e.g., over a duration of time). For example, in such embodiments, the intensity of a signal captured by imaging sensor 142 and/or imaging sensor 144 over a duration of time, which may be associated with light beams 114 emitted by endoilluminator 102 into eye 150 or reflected by eye 150 back into imaging sensor 142 and/or imaging sensor 144, may be utilized to determine the amount of light delivered to eye 150. In further embodiments, the amount of light delivered to eye 150 is determined utilizing photon counting. In certain embodiments, since light intensity decreases as a distance of transmission thereof increases, controller 130 may further take into account a distance of a distal end of endoilluminator 102 to, e.g., retina 152 or a region of retina 152, such as the macula, or a distance of the retina 152 to, e.g., imaging sensor 144. Thus, the distance light beams 114 travel within eye 150 may further inform the determination of the amount of light delivered to eye 150. In certain embodiments, the determination is still further based upon the presence of a dye within the ocular space of eye 150, which may be utilized during certain ophthalmic surgical procedures, such as chromovitrectomies, to aid in the visualization of ocular tissues and anatomic planes. In such embodiments, the dye may obstruct and/or reduce the amount of light delivered to eye 150.

At 230, upon determining the amount of light delivered to eye 150, controller 130 determines if the amount is excessive (e.g., high risk of light-induced damage may occur therefrom). Such determination may be based on artificial intelligence processes, and may take into account several factors. For example, in certain embodiments, the determination at 230 takes into account a light tolerance of, e.g., retina 152 or region of retina 152, such as the macula.

If, at 230, controller 130 determines that the amount of light delivered to eye 150 is not excessive, then controller 130 may continue to monitor the amount of light delivered, repeating operations 220 and 230. If, however, controller 130 determines that the amount of light delivered to eye 150 is excessive, then in certain embodiments, at 240, controller may provide an alert to the surgeon advising that the amount of light delivered to eye 150 is excessive. As described above, the alert may be in the form of an audible alert, a visual alert, and/or a tactile alert. In certain embodiments, the alert is a visual alert displayed on a display device within the operating environment, such as a display device associated with viewing device 140 or a surgical console (e.g., a 3D organic light-emitting diode (OLED) display device), or a head-mounted display or holographic goggles worn by the surgeon. In certain embodiments, the alert is an audible alert sounded by a surgical console or similar device, which may be alternative to or in addition to a visual alert. In certain embodiments, the alert may provide the surgeon with the determined amount of light delivered to eye 150, and/or provide the surgeon with predetermined options for modifying one or more parameters of light beams 114 to reduce phototoxicity thereof, according to predetermined settings associated with light source 110. The surgeon may then, based on either their own selection of settings for light source 110, or by selecting one of the predetermined options provided in the alert, trigger (e.g., through a foot pedal, pressing of an on-screen or analog button, etc.) controller 104 to cause light driver 120 to modify one or more parameters of light beams 114 according to the one or more settings associated with light source 110 to reduce the phototoxicity of light beams 114 (e.g., switch them to a more limited waveform).

Alternatively or in addition to alerting the surgeon, at 240, if controller 130 determines that the amount of light delivered to eye 150 is excessive, controller 130 may automatically cause light driver 120 to modify the one or more parameters of light beams 114 generated by light source 110 according to the predetermined settings of light source 110. In such embodiments, no input from the surgeon is necessary, which may reduce procedural inefficiencies during the ophthalmic surgical procedure, such as requiring the surgeon to pause the procedure to adjust the settings of light source 110.

The one or more parameters of light beams 114 that may be modified by the surgeon or controller 130 to reduce phototoxicity thereof may include parameters of all or certain visible wavelengths of light beams 114. For example, in certain embodiments, the one or more parameters modified include such parameters for all visible wavelengths of light beams 114. In other embodiments, however, the one or more parameters modified include only such parameters for certain visible wavelengths, e.g., more harmful wavelengths such as blue wavelengths between about 450 nm (nanometers) and about 495 nm. In still other embodiments, one or more parameters of different wavelengths of light may be differentially modulated. For example, in such embodiments, harmful blue light may be modulated in a more limiting manner than the remainder of the visible light spectra of light beams 114.

The one or more parameters of light beams 114 include waveform type, duty cycle, pulse rate, pulse width, intensity, etc., of all or certain visible wavelengths of light beams 114. For example, in certain embodiments, the waveform type of all or certain visible wavelengths of light beams 114 may be modified between a sinusoidal waveform, a triangular waveform, a square waveform, etc. In certain embodiments, a total intensity of all visible wavelengths of light beams 114 may be reduced. In certain other embodiments, an intensity of only certain visible wavelengths, e.g., blue wavelengths between about 450 nm and about 495 nm, may be reduced. In certain embodiments, a pulse rate of all visible wavelengths of light beams 114 may be modified. In certain other embodiments, a pulse rate of only blue wavelengths is modified. In embodiments where a pulse rate of light beams 114 is modified, the pulse rate may be set to equal a frame rate of, e.g., imaging device 142 and/or 144, thus enabling undisturbed image capture of illuminated eye 150 while simultaneously reducing the amount of light delivered thereto. Accordingly, the modification of light beams 114 may be visually unperceivable to the surgeon when viewing eye 150 on, e.g., viewing device 140.

Figure 7:
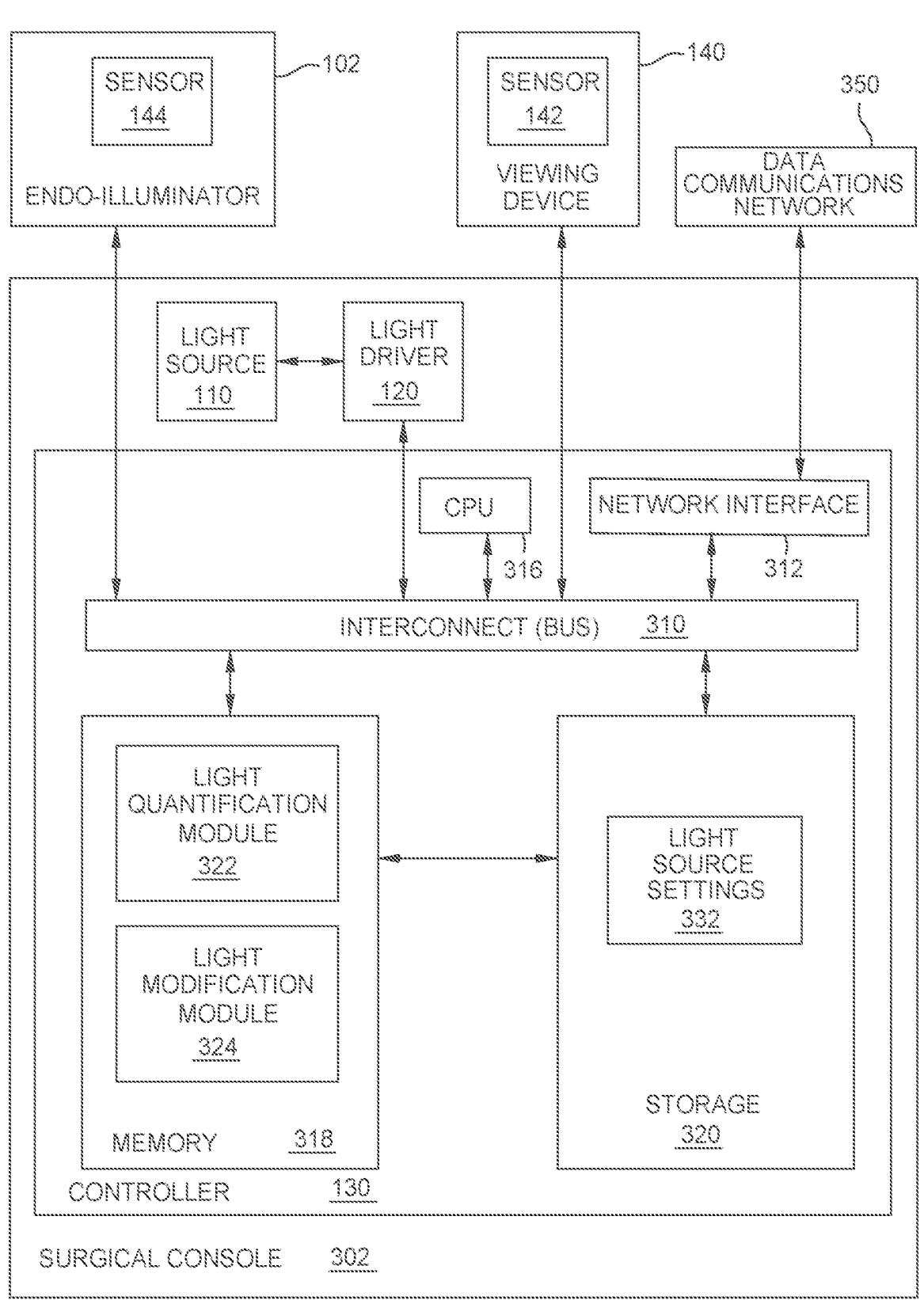
FIG. 7 illustrates exemplary components of the illumination system of FIG. 5, in accordance with certain embodiments of the present disclosure.

FIG. 7 illustrates an exemplary diagram showing how components of illumination system 100, depicted in FIG. 5, communicate and operate together, as well as with other devices utilized during an ophthalmic surgical procedure. As shown, illumination system 100 includes, without limitation, controller 130, light source 110, and light driver 120, which may integrated with surgical console 302. Controller 130 includes interconnect 310 and network interface 312 for connection with data communications network 350. Controller 104 further includes central processing unit (CPU) 316, memory 318, and storage 320. CPU 316 may retrieve and store application data in the memory 318, as well as retrieve and execute instructions stored in the memory 318. Interconnect 310 transmits instructions and application data among CPU 316, network interface 312, memory 318, storage 320, light driver 120, and viewing device 140 and/or endoilluminator 102, etc. CPU 316 can represent a single CPU, multiple CPUs, a single CPU having multiple processing cores, and the like. Memory 318 represents volatile memory, such as random access memory.

Storage 320 may be non-volatile memory, such as a disk drive. Although shown as a single unit, storage 320 may be a combination of fixed or removable storage devices, such as fixed disc drives, removable memory cards or optical storage, network attached storage (NAS), or a storage area-network (SAN). Storage 320 may comprise light source settings 332 and/or mappings of the light source settings 332 to one or more specific circumstances in which the amount of light delivered to eye 150 is determined to be excessive by controller 150. Light source settings 332 may include pre-set instructions for driving light source 110 with the corresponding settings associated with light source 110.

Memory 318 comprises light quantification module 322 that includes instructions, which when executed by CPU 316, allow controller 130 to determine an amount of light delivered to eye 150, based on imaging data from viewing device 140 and/or endoilluminator 102, and whether such amount of light is excessive. In certain embodiments, memory 318 further includes light modification module 324 that includes instructions, which when executed by CPU 316, allow controller 130 to modify, via light driver 120, one or more parameters of light beams 114 generated by light source 110, based on light source settings 332.

As described above, embodiments of the present disclosure provide an illumination system configured to automatically quantify or calculate the amount of light delivered to an eye during an ophthalmic surgical procedure, which may be more accurate than current methods assuming a fixed distance of endoillumination and fixed intensity of illumination light. In certain aspects, if the quantified amount of light is determined to be excessive and therefore, reaching phototoxic levels, the illumination system may automatically modify the illumination light to reduce phototoxicity thereof. In certain aspects, if the quantified amount of light is determined to be excessive, the illumination system may alert a surgeon that the amount of light delivered is excessive, so that the surgeon may trigger modification of the illumination light. By modifying the illumination light to reduce phototoxic effects thereof, the risk of injury to the patient's eye may be reduced, improving the overall safety of the ophthalmic procedure.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

Within a claim, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) unless the element is expressly recited using the phrase "means for" or, in the case of a method claim, the element is recited using the phrase "step for." The word "exemplary" is used herein to mean "serving as an example, instance, or illustration." Any aspect described herein as "exemplary" is not necessarily to be construed as preferred or advantageous over other aspects.

In some embodiments, an illumination system comprises a light source configured to generate a light beam for illuminating an ocular space, the light source comprising: a light driver in data communication with a system controller and configured to drive the light source to generate the light beam; and the system controller, comprising: a memory comprising executable instructions; and a processor in data communication with the memory and configured to execute the instructions to cause the illumination system to: determine an amount of light delivered to a tissue within the ocular space, the determination at least partially based on data received from an imaging system associated with the system controller and light source; determine if the amount of light delivered to the tissue is excessive; and, if the amount of light delivered to the tissue is determined to be excessive, provide an alert to a user that the amount of light delivered to the tissue is excessive. In some embodiments, the alert is a visual alert displayed on a display device of a surgical console. In some embodiments, the alert is a visual alert displayed on a display device worn by the user. In some embodiments, the alert is an audio alert sounded by a surgical console.

In some embodiments, a system for quantifying light exposure of a patient retina during an ophthalmic procedure, the system comprising: a light source configured to illuminate the patient retina with directed light during the ophthalmic procedure to thereby produce an illuminated retina surface; a camera configured to collect image data of the illuminated retina surface as collected image data; an indicator device; and an electronic control unit (ECU) in communication with the indicator device and the camera, wherein the ECU is configured to: receive the collected image data from the camera depicting the illuminated retina surface; estimate a cumulative energy spectral density of the directed light falling incident upon the retina during the ophthalmic procedure using the collected image data; and execute a control action indicative of possible light toxicity in response to the cumulative energy spectral density exceeding a light toxicity threshold, including activating the indicator device. Further, the ECU is in communication with the light source and is configured to receive light output data therefrom, the light output data being descriptive of an intensity and spectral content of the light illuminating the patient retina. In some embodiments, the ECU is configured to divide the illuminated retina surface into multiple virtual zones, and to map the cumulative energy spectral density to the illuminated retina surface such that each one of the multiple virtual zones has a corresponding cumulative energy spectral density. In some embodiments, the light toxicity threshold includes a plurality of zone-specific light toxicity thresholds, and wherein the ECU is configured to determine, from the cumulative energy spectral density, a respective cumulative energy spectral density for each of the multiple zones, and to thereafter execute the control action in response to the respective cumulative energy spectral density of one the multiple virtual zones exceeding a corresponding one of the zone-specific light toxicity thresholds. In some embodiments, the indicator device includes a speaker, and wherein the control action includes sounding an audible alarm via the speaker. In some embodiments, the indicator device includes a color-coded lamp, and wherein the control action includes illuminating the color-coded lamp. In some embodiments, the indicator device includes a display screen, and wherein the control action includes displaying information via the display screen indicative of the cumulative energy spectral density. In some embodiments, the ECU is configured to display a heat map of the illuminated retina surface via the display screen, the heat map being indicative of a distribution of the cumulative energy spectral density across the illuminated retina surface. In some embodiments, the digital image data includes a fundus image of the patient retina, and wherein the heat map is displayed on the fundus image, such that the fundus image forms a backdrop for the heat map. In some embodiments, the ECU is configured to selectively adjust a control setting of the light source, and wherein the control action includes adjusting, as the control setting, a wavelength and/or an intensity level of the directed light in real-time during the ophthalmic procedure. In some embodiments, the light source is a light pipe or an endoilluminator having a variable intensity and/or spectral content.

In some embodiments, a method for quantifying light exposure of a patient retina during an ophthalmic procedure, the method comprising: illuminating the patient retina with directed light from a light source during the ophthalmic procedure to thereby produce an illuminated retina surface; collecting image data of the illuminated retina surface, as collected image data, using a camera; receiving the collected image data from the camera via an electronic control unit (ECU); estimating a cumulative energy spectral density, via the ECU, of the directed light falling incident upon the retina during the ophthalmic procedure; and in response to the cumulative energy spectral density exceeding a light toxicity threshold, executing a control action via the ECU, wherein the control action is indicative of possible light toxicity, the control action including activating an indicator device. In some embodiments, the method further comprises dividing the illuminated retina surface via the ECU into multiple virtual zones; and mapping the cumulative energy spectral density to the illuminated retina surface via the ECU, such that each one of the multiple zones has a corresponding cumulative energy spectral density. In some embodiments, the light toxicity threshold includes a plurality of zone-specific light toxicity thresholds, and the method further comprises executing the control action via the ECU in response to the respective cumulative energy spectral density of one the multiple virtual zones exceeding a corresponding one of the zone-specific light toxicity thresholds. In some embodiments, the method further comprises receiving light output data from the light source, via the ECU, the light output data being descriptive of an intensity and spectral content of directed light emitted by the light source when illuminating the patient retina, wherein estimating the cumulative energy spectral density includes using the intensity and spectral content from the light output data. In some embodiments, the indicator device includes a speaker and a color-coded lamp, and wherein executing the control action includes sounding an audible alarm via the speaker and illuminating the color-coded lamp. In some embodiments, the indicator device includes a display screen, and wherein the control action includes displaying a heat map via the display screen indicative of the cumulative energy spectral density, the heat map being indicative of a distribution of the cumulative energy spectral density across the illuminated retina surface. In some embodiments, executing the control action includes selectively adjusting a control setting of the light source via the ECU, the control setting including a wavelength and/or an intensity level of the directed light.

In some embodiments, an electronic control unit (ECU) for quantifying light exposure of a patient retina during an ophthalmic procedure, the ECU being in communication with a light source during the ophthalmic procedure to thereby produce an illuminated retina surface, the ECU comprising: a processor; input/output (I/O) circuity in communication with the processor, the light source, an indicator device, and a camera; and memory on which is recorded computer-readable instructions, wherein execution of the computer-readable instructions by the processor causes the ECU to: receive collected image data from the camera during the ophthalmic procedure, wherein the collected image data depicts an illuminated retina surface of the patient retina; receive light output data from the light source, the light output data being descriptive of an intensity and spectral content of directed light emitted by the light source when illuminating the patient retina; calculate a cumulative energy spectral density of the directed light from the light source providing the illuminated retina surface during the ophthalmic procedure; and execute a control action indicative of possible light toxicity in response to the cumulative energy spectral density exceeding a light toxicity threshold, including activating the indicator device. In some embodiments, execution of the computer-readable instructions by the processor causes the ECU to: divide the illuminated retina surface into multiple virtual zones; and map the cumulative energy spectral density to the illuminated retina surface such that each one of the multiple virtual zones has a corresponding cumulative energy spectral density, wherein the light toxicity threshold includes a plurality of zone-specific light toxicity thresholds, and wherein the ECU determines, as the cumulative energy spectral density, a respective cumulative energy spectral density for each of the multiple virtual zones, and thereafter executes the control action in response to the respective cumulative energy spectral density of one the multiple virtual zones exceeding a corresponding one of the zone-specific light toxicity thresholds.

The detailed description and the drawings are supportive and descriptive of the disclosure, but the scope of the disclosure is defined solely by the claims. While some of the best modes and other embodiments for carrying out the claimed disclosure have been described in detail, various alternative designs and embodiments exist for practicing the disclosure defined in the appended claims. Furthermore, the embodiments shown in the drawings or the characteristics of various embodiments mentioned in the present description are not necessarily to be understood as embodiments independent of each other. Rather, it is possible that each of the characteristics described in one of the examples of an embodiment can be combined with one or a plurality of other desired characteristics from other embodiments, resulting in other embodiments not described in words or by reference to the drawings. Accordingly, such other embodiments fall within the framework of the scope of the appended claims.

What is claimed is:

1. An illumination system, comprising:
   a light source configured to generate a light beam for illuminating an ocular space, the light source comprising:
   a light driver in data communication with a system controller and configured to drive the light source to generate the light beam; and
   the system controller, comprising:
   a memory comprising executable instructions; and
   a processor in data communication with the memory and configured to execute the instructions to cause the illumination system to:
   determine an amount of light delivered to a tissue within the ocular space, the determination at least partially based on data received from an imaging system associated with the system controller and light source; and
   modify with the light driver, based on the determined amount of light delivered to the tissue within the ocular space, at least one parameter associated with the light beam generated by the light source, wherein the at least one parameter comprises at least one of waveform type, pulse rate, pulse width, and pulse repetition frequency (PRF);
   wherein the modification of the at least one parameter of the generated light beam is further based upon a light tolerance of the tissue within the ocular space.

2. The illumination system of claim 1, wherein the determination of the amount of light delivered to the tissue within the ocular space is further based on a distance between a distal end of a probe associated with the light source and the tissue within the ocular space, and wherein the distal end of the probe comprises a sensor communicatively coupled to the system controller.

3. The illumination system of claim 1, wherein the determination of the amount of light delivered to the tissue within the ocular space is further based on a duration of time that the light is delivered to the tissue within the ocular space.

4. The illumination system of claim 1, wherein the determined amount of light is a cumulative delivered light (CDL).

5. The illumination system of claim 1, wherein the determined amount of light is a macular cumulative delivered light (mCDL).

6. The illumination system of claim 1, wherein the at least one parameter of the generated light beam comprises a duty cycle of the generated light beam.

7. The illumination system of claim 6, wherein the duty cycle of the generated light beam is modified to a square waveform.

8. The illumination system of claim 7, wherein the duty cycle of the generated light beam is modified to a sinusoidal waveform.

9. The illumination system of claim 1, wherein the at least one parameter of the generated light beam comprises a total intensity of the generated light beam.

10. The illumination system of claim 1, wherein the at least one parameter of the generated light beam comprises an intensity of wavelengths of light of the generated light beam between about 450 nm and about 495 nm (blue wavelengths).

11. The illumination system of claim 1, wherein determining the amount of light delivered to a tissue within the ocular space comprises photon counting.

12. The illumination system of claim 11, wherein the pulse rate comprises a pulse rate of wavelengths of light of the generated light beam between about 450 nm and about 495 nm (blue wavelengths).

13. The illumination system of claim 11, wherein the instructions are further executable to cause the illumination system to set the pulse rate to approximately equal a frame rate of an imaging sensor receiving the light beam for imaging the ocular space.

14. The illumination system of claim 1, wherein modification of the at least one parameter of the generated light beam is further based upon a presence of a dye within the ocular space.

* * * * *